United States Patent
Lowe

(10) Patent No.: US 9,662,184 B2
(45) Date of Patent: *May 30, 2017

(54) VIBRATING DENTAL DEVICES

(71) Applicant: OrthoAccel Technologies, Inc, Bellaire, TX (US)

(72) Inventor: Michael K. Lowe, Bellaire, TX (US)

(73) Assignee: OrthoAccel Technologies, Inc., Bellaire, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/186,958

(22) Filed: Jun. 20, 2016

(65) Prior Publication Data

US 2016/0296300 A1    Oct. 13, 2016

Related U.S. Application Data

(63) Continuation of application No. 14/612,121, filed on Feb. 2, 2015, now Pat. No. 9,370,405, which is a continuation of application No. 12/615,049, filed on Nov. 9, 2009, now Pat. No. 9,028,250, which is a continuation-in-part of application No. 11/773,849, filed on Jul. 5, 2007, application No. 15/186,958, which is a continuation of application No. 14/612,127, filed on Feb. 2, 2015, now Pat. No. 9,370,406, which is a continuation of application No.
(Continued)

(51) Int. Cl.
| | |
|---|---|
| *A61C 3/00* | (2006.01) |
| *A61C 7/00* | (2006.01) |
| *A61C 7/08* | (2006.01) |
| *A61C 7/12* | (2006.01) |
| *A61C 1/00* | (2006.01) |

(52) U.S. Cl.
CPC ............... *A61C 7/008* (2013.01); *A61C 7/00* (2013.01); *A61C 7/08* (2013.01); *A61C 7/12* (2013.01); *A61C 1/0015* (2013.01); *A61C 7/002* (2013.01); *A61C 2204/005* (2013.01)

(58) Field of Classification Search
CPC .. A61C 7/008; A61C 7/08; A61C 7/00; A61C 7/36
USPC .......................... 433/6, 18, 24, 118, 119, 122
See application file for complete search history.

(56) References Cited

U.S. PATENT DOCUMENTS

| | | | | |
|---|---|---|---|---|
| 1,826,434 A | * | 10/1931 | Reiss ..................... | A61C 17/20 601/86 |
| 4,123,844 A | * | 11/1978 | Kurz ....................... | A61C 7/06 433/5 |
| 4,244,688 A | | 1/1981 | Kurz et al. | |

(Continued)

FOREIGN PATENT DOCUMENTS

| | | | |
|---|---|---|---|
| EP | 1280261 | 1/2003 | |
| WO | WO 2005107638 A1 * | 11/2005 | ........... A61C 19/003 |

*Primary Examiner* — Matthew Nelson
(74) *Attorney, Agent, or Firm* — Boulware & Valoir

(57) ABSTRACT

A faster method of orthodontic remodeling for a patient wearing a vibrating orthodontic remodeling device for about 20 minutes a day to accelerated tooth movement is described. The vibrating orthodontic remodeling device has an extraoral housing containing a power source operably coupled to an actuator that is operably coupled to a processor that controls the actuator, and is connected to an intraoral U-shaped bite plate. The device is held in place during use by the teeth clamping on the bite plate.

27 Claims, 7 Drawing Sheets

Related U.S. Application Data

12/615,049, which is a continuation-in-part of application No. 11/773,849.

(60) Provisional application No. 60/906,807, filed on Mar. 14, 2007.

(56) References Cited

U.S. PATENT DOCUMENTS

| | | | |
|---|---|---|---|
| 4,348,177 A | 9/1982 | Kurz et al. | |
| 4,382,780 A | 5/1983 | Kurz et al. | |
| 4,764,111 A * | 8/1988 | Knierim | A61C 7/06 340/309.7 |
| 5,030,098 A * | 7/1991 | Branford | A61H 23/00 433/215 |
| 5,554,971 A | 9/1996 | Foster | |
| 5,774,425 A * | 6/1998 | Ivanov | G07C 3/04 368/11 |
| 5,780,958 A | 7/1998 | Strugach | |
| 5,967,784 A * | 10/1999 | Powers | A61C 7/00 433/2 |
| 6,089,864 A | 7/2000 | Buckner | A61F 5/56 433/6 |
| 6,613,001 B1 * | 9/2003 | Dworkin | A61C 7/00 600/590 |
| 6,632,088 B2 | 10/2003 | Voudouris | |
| 6,684,639 B2 | 2/2004 | Ichinose | |
| 6,832,912 B2 * | 12/2004 | Mao | A61C 7/22 433/24 |
| 6,870,304 B2 | 3/2005 | Magnussen | |
| 7,029,276 B2 * | 4/2006 | Mao | A61C 7/22 433/24 |
| 7,296,318 B2 * | 11/2007 | Mourad | A46B 15/0002 15/22.1 |
| 7,511,454 B1 | 3/2009 | Legg | |
| 8,152,521 B2 | 4/2012 | Yamamoto | |
| 2004/0013993 A1 * | 1/2004 | Ito | A61C 7/08 433/6 |
| 2004/0063073 A1 * | 4/2004 | Kajimoto | A61N 7/00 433/215 |
| 2006/0287620 A1 | 12/2006 | Tseng | |
| 2007/0103016 A1 | 5/2007 | Park | |
| 2007/0161461 A1 | 7/2007 | Nguyen | |
| 2007/0161931 A1 | 7/2007 | Kunita | |
| 2007/0179414 A1 | 8/2007 | Imboden | |
| 2007/0208284 A1 | 9/2007 | Huang | |
| 2007/0255188 A1 | 11/2007 | Tseng | |
| 2007/0299372 A1 | 12/2007 | Chang | |
| 2008/0129130 A1 | 6/2008 | Mun | |
| 2008/0227046 A1 | 9/2008 | Lowe | |
| 2008/0227047 A1 | 9/2008 | Lowe | |
| 2008/0233541 A1 * | 9/2008 | De Vreese | A61C 19/066 433/216 |
| 2009/0051312 A1 | 2/2009 | Simon | |
| 2009/0058361 A1 | 3/2009 | John | |
| 2009/0224616 A1 | 9/2009 | An | |
| 2010/0055634 A1 | 3/2010 | Spaulding | |

* cited by examiner

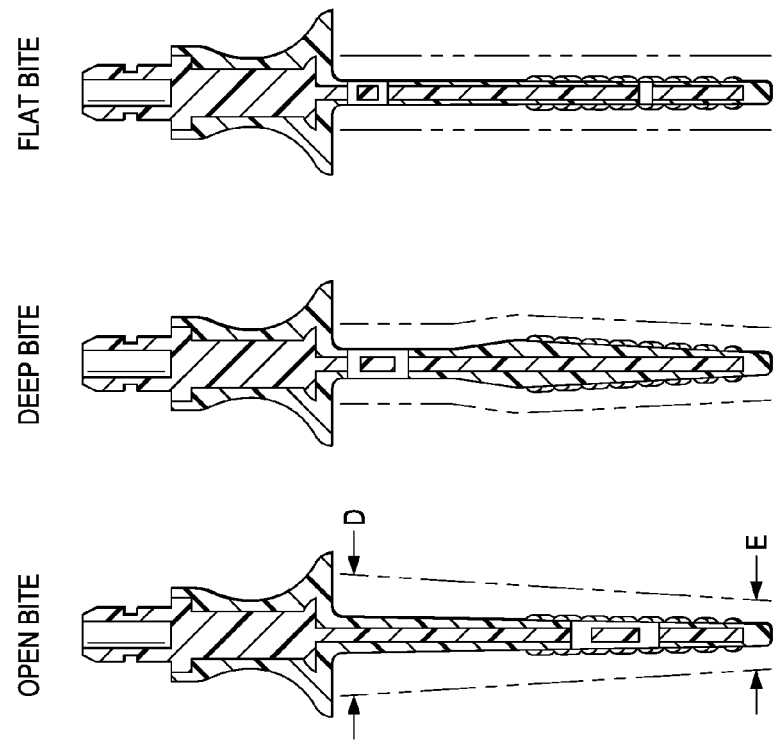
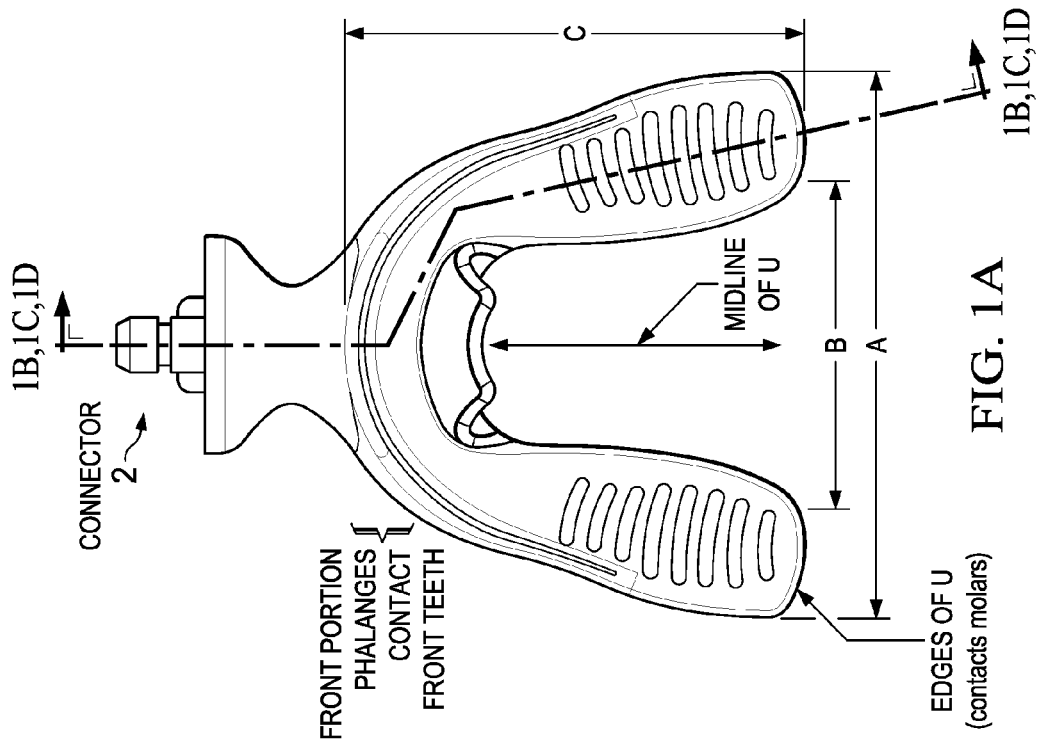
FIG. 1A
FIG. 1B
FIG. 1C
FIG. 1D

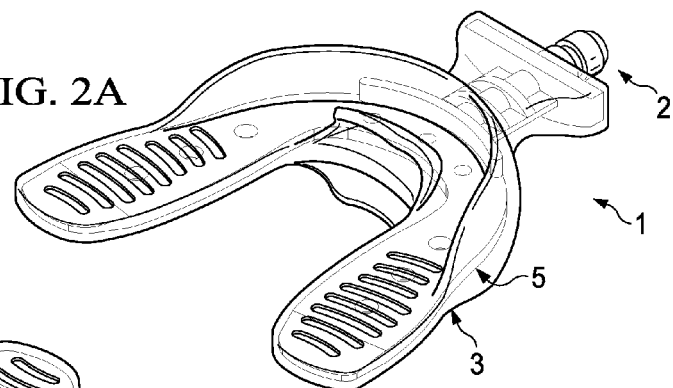
FIG. 2A
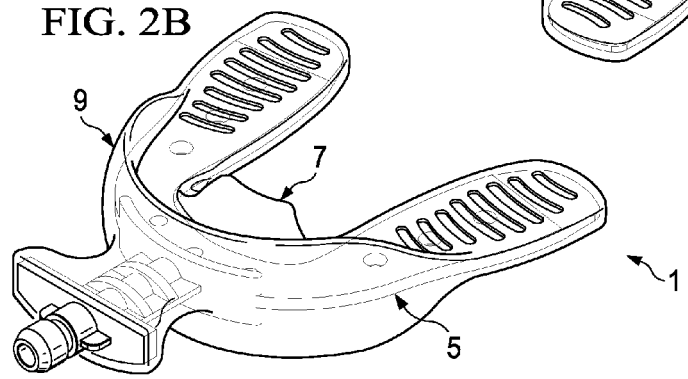
FIG. 2B
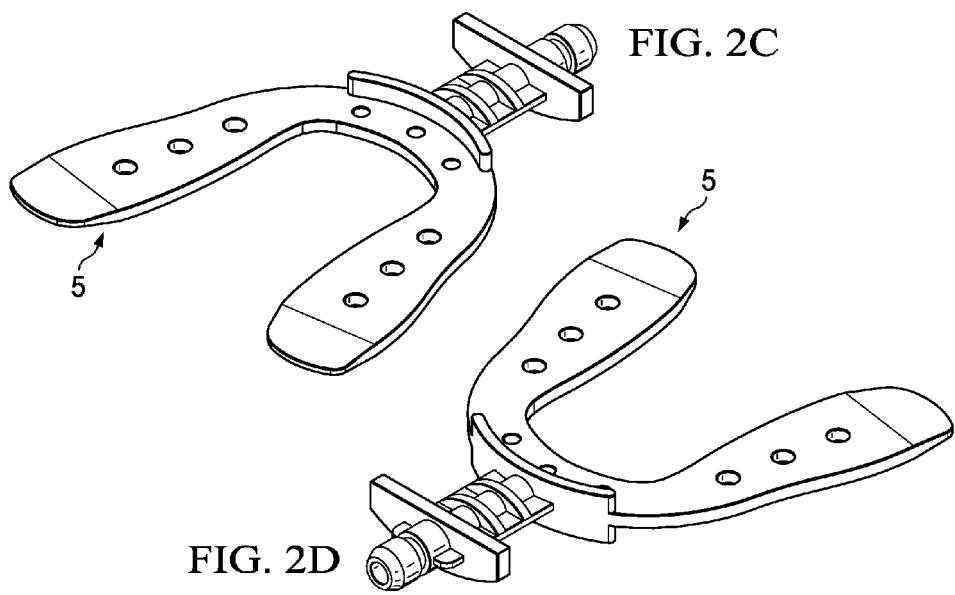
FIG. 2C
FIG. 2D

VIBRATING DENTAL DEVICES

PRIOR RELATED APPLICATIONS

This application is a Continuation of Ser. Nos. 14/612,121 and 14/612,127, both of which were filed Feb. 2, 2015 and are Continuations of Ser. No. 12/615,049, filed Nov. 9, 2009, which is a Continuation-in-Part of US2008227046 (Ser. No. 11/773,849), filed Jul. 5, 2007, which claims priority to 60/906,807, filed Mar. 14, 2007. Each of these is incorporated by reference in their entirety for all purposes.

FEDERALLY SPONSORED RESEARCH STATEMENT

Not applicable.

REFERENCE TO MICROFICHE APPENDIX

Not applicable.

FIELD OF THE DISCLOSURE

The invention relates to vibrating dental devices for correcting malocclusion.

BACKGROUND OF THE DISCLOSURE

Orthodontics is a dental specialty that treats malocclusion through the movement of teeth as well as control and modification of facial growth. This process is usually accomplished by using a continuous mechanical force to induce bone remodeling, thereby enabling the teeth to move to a better position. In this approach, orthodontic appliances provide a continuous static force to the teeth via an archwire connected to brackets affixed to each tooth or via a removable appliance such as an aligner, or some similar accessory, that fits over the dentition. As the teeth slowly move due to the force, the force is dissipated. The archwires are adjusted to add additional force and to continue the desired tooth movement. Although effective, this widely accepted approach takes about twenty four months on average to achieve success.

Dental researchers have long postulated that a pulsating force might also be used to move teeth more rapidly and to ease the discomfort of traditional orthodontics.

Mao was probably the first to prove that the use of cyclic forces could improve dental straightening in rabbits (see U.S. Pat. No. 6,684,639, U.S. Pat. No. 6,832,912, U.S. Pat. No. 7,029,276). Certain dynamic loading patterns (cycling force with rest periods) were shown to greatly increase bone formation compared to basic dynamic loading. Inserting rest periods is now known to be especially efficacious as it allows mechanosensitivity to be restored to the bone tissue. A point of diminishing returns is reached within each loading session. Therefore, intermittently loading cyclic force can increase the rate of bone formation significantly.

U.S. Pat. No. 4,244,688, U.S. Pat. No. 4,348,177, and U.S. Pat. No. 4,382,780 describe devices used to vibrate the teeth during orthodontic treatment, although each uses a different means of applying a vibration. The U.S. Pat. No. 4,244,688 employs a cumbersome external power source to power one to four small motors, whereas U.S. Pat. No. 4,348,177 uses pulsating fluids moved with the chewing motion of the jaw, and U.S. Pat. No. 4,382,780 uses a radio and speaker to set up a vibration. These devices are mounted on a bulky headgear that surrounds the head and are connected directly to the teeth by its intraoral portions. The devices are cumbersome, difficult to construct, expensive and are very difficult to use, thus reducing patient compliance.

U.S. Pat. No. 5,030,098 by Branford describes a handheld device that simulates chewing in order to treat periodontal disease by increasing blood flow to the gums. The mouthpiece has a perforated malleable plate such that biting of the mouthpiece results in the plate adapting to the user's bite which, of course, varies with each user. The external vibrator imparts motion to the mouthpiece and thus the user's teeth. The device, however, uses an external power source and vibrator. Further, the dental plate is brass, and is very unpleasant to bite on, thus necessitating a second exterior coating and further complicating manufacture and cost.

U.S. Pat. No. 5,967,784 by Powers describes a similar device to that described by Branford. It too is a hand-held tooth vibrator that is simple and has an exterior motor housing connected to a vibrating interdental mouthpiece portion for gripping between the teeth of the patient. The exterior housing contains a battery and a switch for selectively operating a motor with an off-center weight attached to the motor rotating shaft for creating a high frequency vibration that vibrates the entire device. The mouthpiece is disposable, making the system affordable and more convenient to use. The patent teaches using the device to alleviate pain by inserting the interdental mouthpiece between the teeth and clenching and releasing the teeth over the mouthpiece, in an attempt to engage as many teeth as possible in the transmitted vibrations. The vibration is believed to alleviate discomfort by increasing blood flow.

The devices of Branford and Powers seem superficially similar to those of the invention herein. However, there is no recognition in either patent that the vibratory device can be used for alveolar bone remodeling or more rapid tooth movement. Furthermore, the shape of the dental plate in each case is a very flat U- or Y-shaped member that is largely ineffective for remodeling dentoalveolar bone. Additionally, the vibration is not optimized in frequency and amplitude for remodeling. Finally, neither device is entirely intraoral, and the extraoral component may cause drooling and inhibit patient compliance. The extraoral component may also lead to inhibition about use of the device in certain settings. All of these shortcomings reduce the effectiveness of these devices for craniofacial remodeling uses.

U.S. Pat. No. 6,632,088 describes a bracket with powered actuator mounted thereto to provide vibration, but this device is cumbersome, and thus may affect patient comfort and ultimately patient acceptance of the device. Further, the device locks to the bracket and archwire, and vibration of the tooth through the bracket is less than optimal, causing wear to the tooth enamel and causing discomfort.

WO2007116654 describes another intraoral vibrating mouthpiece, but the mouthpiece is complex, designed to fit over the teeth and will be expensive to manufacture. Further, to the extent that this device vibrates the brackets, it suffers from the same disadvantages above.

SUMMARY OF THE DISCLOSURE

The invention generally relates to improved devices for dental remodeling through the application of cyclic forces. There are four main embodiments herein described as well as several variations thereon: 1) a variety of bite plate designs to accommodate common patient morphologies; 2)

an improved extraoral vibrator with improved performance characteristics; 3) a bite plate connector; and 4) a completely intraoral bite plate.

In a first embodiment, the invention is an improved bite plate design that accommodates the various bite configurations that a patient may have. Thus, a wedge-shaped bite plate sloping with increased vertical dimension from anterior to posterior is provided for patients with a deep-bite malocclusion; a wedge-shaped bite plate sloping with increased vertical dimension from posterior to anterior is provided for patients with an open-bite; and a flat bite plate is provided for patients with malocclusion that does not involve an open-bite or deep-bite (see also FIG. 1).

In a second embodiment, the improved extraoral vibrator has a more stable vibrator with improved performance characteristics of decreased sound and low variability frequency and force. In particular, the improved vibrator has a noise level less than 55 dB when measured at 6 inches, a frequency at 20-40 Hz, with a variance of only 2 Hz, and a force of 0.1-0.5 Newtons, with a variance of ±0.05 N.

In preferred embodiments, vibrating dental devices have the capability of recording device usage and reporting same to the dental professional. Preferably these communications are wireless, e.g., via Bluetooth®, but can also be wired, and the communication can occur in the dental professional's office or via the internet. In another embodiment, the dental professional (and possibly patient) has the ability to modulate frequency, force, and which vibrators are used, as needed for patients with sensitivity to a high frequency X force combinations, and who need to vibrate certain teeth and omit others. Designing circuitry and programming for achieving these goals is well within the art, and is further described in US2008227046.

In other embodiments, the bite plate contains a chip with a short sound recording, such as is found in greeting cards and toys. The recording can be activated with, e.g., a depressible switch, and can be pre-recorded to indicate e.g., plate size, or can be recorded by the dental professional with e.g., a short message for the patient. Alternatively, plate size can be included on a chip within the plate which then can be read with a scanner, e.g., as is done with RFID scanners.

In other embodiments, the external housing of any dental device is customizable by printing thereon particular colors and/or designs, as specified by each customer. Alternatively, a reasonable range of colors and text or logo printing options may be available from which the customer can choose.

In other embodiments, the each device is printed with a unique serial number and/or bar codes to allow for device tracking.

In a third embodiment, an improved connector is provided for connecting the bite plate to an extraoral vibrator, wherein the connector is asymmetric and thus prevents the user from inserting the plate upside down. The connector comprises a flare at the midline of the bite plate with depressions therein so that the matching protrusions on the vibrator fit thereinto. The depressions are offset from the central axis of the connector, thus the connector cannot be accidentally inserted upside down. The flare has a cylindrical shaft protruding therefrom for insertion into an appropriately shaped receptacle on the vibrator. The shaft has matching pins or protrusions on each side of the shaft, at the end near the bite plate, and there are corresponding depressions in the receptacle on the vibrator. This particular connector is a snap fit connector, configured so that only manual force is needed to insert and remove the bite plate. The snap fit in this instance is accomplished with a groove on the cylindrical shaft into which a circular spring in the vibrator will fit into. The application of a small amount of force stretches the spring slightly, allowing the device to be removed.

In a fourth major embodiment, the invention generally relates to a completely intraoral vibrating dental plate, wherein the entire device is contained in a thin, roughly planar, dentition shaped plate, and is hermetically sealed. All intraoral bite plate embodiments may be combined with the improved bite plate designs shown and discussed in FIG. 1. In its simplest embodiment, one or more vibrators are mounted on a bite plate and hermetically sealed. The device is then wirelessly activated with an external power source, such as that described in US2009058361 and all programming components are also external.

In another embodiment of the intraoral device, a battery is also placed on the bite plate, together with on/off switches on the plate, which can be, for example, activated by biting the plate.

For patient comfort, the smallest means of providing vibration are employed on the intraoral device. A large number of very small vibrating motors are available, as shown in the table below, but piezoelectric motors may be preferred due to the small size, and off-set weighted motors may be preferred due to low cost and availability. Particularly preferred are the substantially planar motors where the vibration is substantially parallel to the substrate (e.g, U.S. Pat. No. 5,554,971, U.S. Pat. No. 5,780,958, US2009224616, US2008129130, US2007103016, WO0178217, each incorporated by reference).

| Company | Catalog | Size | Specifications |
|---|---|---|---|
| ELLIPTEC AG ™ | NA See U.S. Pat. No. 6,870,304 | 10 × 3 × 2 mm | 3-6 volts piezoelectric motor |
| SURPLUS TRADERS ™ | MF820 | 8 × 4 mm (0.315 × 0.1575 inches) | 1.5 to 4.5 VDC weighted shaft |
| SURPLUS TRADERS ™ | MF918 | 0.45 × 0.16 inches | 1 VDC to 5 VDC 18 ohms Weighted shaft |
| MOTOROLA ™ | G13566 | 0.44 × 0.18 inches | 1 VDC to 9 VDC 10 ohms Weighted shaft |
| SURPLUS TRADERS ™ | MF835 | 0.45 × 0.24 inches | 1.3 Vdc 100 mA Weighted shaft |
| MATSUSHITA ™ | V0296A | 0.24 inch diameter | 1.5 VDC Weighted shaft |

-continued

| Company | Catalog | Size | Specifications |
|---|---|---|---|
| SURPLUS TRADERS ™ | ME235 | 0.24 × 0.5 inches | 1.5 to 3 VDC<br>62 mA<br>weighted shaft |
| PRECISION MICRODRIVES ™ | 304-002 | 4 m × 8 mm | 2.3 VDC to 3.6 VDC<br>100-120 mA<br>11000 rpm<br>Weighted shaft |
| PRECISION MICRODRIVES ™ | 308-100 | 3.4 × 8 | 2.-3.3 V, 120 mA<br>12000 rpm<br>8 mm Shaftless Vibration Motor |

In addition to electromagnetic motors and piezoelectric motors, other motor types can be used including mechanical actuators, ultrasonic motors and the like. Vibrations may be oscillating, random, directional, circular, and the like. Vibrators are well within the skill of the art, and several are described in the patent literature (and commercially available as seen above). For example, US2007299372, US2007255188, US2007208284, US2007179414, US2007161931, US2007161461, US2006287620, each incorporated by reference, describes various vibrator motors.

Batteries may drive the vibrational source for some intraoral embodiments. Small coin batteries, alkaline or lithium, are preferred due to their small size, but hydrogen batteries may also be preferred due to their power and power density, particularly as size and cost decrease with further technological development.

For certain embodiments, a battery that can be wirelessly recharged is preferred for longer product life (e.g., US2009051312, U.S. Pat. No. 7,511,454), but in other embodiments a low cost device is manufactured that is intended to be disposable. It is known in the art to select an appropriate power source/motor combination to provide an orthodontic vibrator that vibrates within the frequency and power suitable for orthodontic remodeling.

Any off the shelf on/off switch can be used. Particularly preferred for the intraoral device is an on/off switch with depressible activator (push button or rocker).

Generally speaking, the vibrator(s), and optional battery, on/off switch and circuitry are placed directly on the bite plate and hermetically sealed with no extraoral protrusions, thus allowing the most compact bite plate, preventing drooling and maximizing patient compliance. In preferred embodiments, the core may contain depressions therein for fitting various components thereinto, thus maintaining the generally planar surface of the bite plate and maintaining a thin cross section.

The bite plate (whether for the intraoral embodiment or not) should have an average thickness of less than 10 mm and preferably is less than 7, 5, 4 or 3 mm. The various components (if any) can be placed anywhere on the bite plate, but preferably the switch is positioned near the molars, where good contact with teeth is easily made, and the vibrators are balanced on each side of the plate.

One or more vibrators can be placed on the plate, e.g., one on each side, or one for each of three tridents or four quadrants, as shown in FIG. 5. Where more than one vibrator is used, the vibrators should be synchronized when in use, so that the vibrations do not cancel each other out. In the alternative, the various portions of the bite plate can be separated with a thin divider portion of elastomeric material that serves to dampen the vibration and prevent its transfer to another portion of the bite plate. Either embodiment can be provided with control circuitry to either synchronize the motors, or to use the motors individually, thus vibrating only certain teeth.

The dental plate itself generally contains a stiff core, such as metal or rigid plastic onto which are placed the vibrator, and optional on/off switch, battery and the circuitry, as needed to run the device. Other stiff core materials can also be employed including ceramic, polymers and resins. However, aluminum and steel are preferred as easy to work with, inexpensive and having some flex, although certain plastic materials, such as polycarbonate, may be preferred as inexpensive and easily molded to fit components.

The dental plate can then be covered with a liquid-tight, elastic polymeric material to protect the user's teeth from the metal, to isolate any electrical components, and to provide a biocompatible and pleasant mouth feel. This is important for an intraoral embodiment, but the coating is optional on an extraoral device. Coatings, such as silicone rubber, polyethylene (PE), high density PE (HDPE), polycarbonate, polyurethane, polypropylene (PP), polyvinylchloride (PVC), polymethyl methacrylate, polyvinylidene fluoride, polyesters, acrylics, vinyl, nylon, rubber, latex, Teflon, or similar material, and combinations thereof may be used.

Preferably, the coating will not have an objectionable taste and will be FDA approved, such as silicone rubber, polypropylene, HDPE, and the like. In another embodiment the bite plate coating and other parts of the appliance that contact oral tissues have a selection of flavorings for additional comfort in use of the appliance. In yet another embodiment, the device is coated with a polymer that can be reshaped for custom fit, such as boil and bite polymers, or polymers that can be activated, cured and/or set with the addition of light and/or chemicals.

Depending on which teeth or regions of dentition that need to be treated, different dental plate shapes are possible. However, generally, the dental plate is flat to allow contact of the occlusal surfaces of all teeth when the dentition has reached a final level plane and U-shaped. Alternatively, the dental plate may cover only a portion of the dentition, thus being restricted to fewer teeth in use and differential tooth movement as a planned treatment approach. The dental plate can also have one or more vertical edges or phalanges (perpendicular to the midline when positioned inside the mouth), said edges being positioned to contact the facial and lingual surfaces of the teeth and possibly even apically beyond the gum line, thus providing increased circulation to the gums. In preferred embodiments, the dental plate has a U-shaped bite plate, and is slightly tapered to be thinner in the back of the mouth to accommodate the hinged nature of the teeth. In other preferred embodiments a series of bite plates such as described in FIG. 1 are provided.

A series of bite plates for sizing a patients bite are also provided. For example, the six bite plates of FIG. 1 can be packaged into a sizing kit for dental use. The sizes can be labeled thereon, or the plates can be color coded or otherwise distinguished with visible markings. Alternatively, as described above a chip containing size information can be read by scanner, or a sound recording can be activated to indicate size information. The sizing tray can contain any number of different sizes including 2, 3, 4, 6, 8, 10 and higher. Preferably, the sizing tray is shaped to display the bite plates in a horizontal configuration (U-shape showing) and allow any fluids, as used during the sterilization or disinfection process, to drain from the surface of the bite plate.

The devices can be used alone, or in combination with other orthodontic devices. In some embodiments, the appliance can be used to speed boney remodeling in orthodontic uses with traditional orthodontic fixed appliances or aligner based treatments or any other appliance used for tooth movement. In other embodiments the appliance can be used to enhance boney remodeling in periodontal and oral surgical uses.

The device of the invention can be used in a variety of oral and maxillofacial applications including malocclusion, trauma repair, temporomandibular joint and muscle disorders (TMIDs), Lefort and other skeletal facial fractures, craniofacial anomalies such as boney clefts, bone defects, dentofacial deformities, dental implants, periodontal bone grafts as well as tooth, muscle, nerve, tendon, ligament, bone, and connective tissue repair.

Thus, the invention also includes a method for movement of one or more teeth by applying differential vibration to selected areas of a bite plate at frequencies between 1 to 1000 Hz (preferably 10-100 Hz and most preferred 20-40 Hz) and a force of 0.01-2 Newtons (or 0.1-0.5 or 0.2 Newtons) for a period of 1-60 minutes, preferably about 1-30 or 1-10 minutes or 20 minutes. This is followed by a period of recovery, ranging from 2-24 hours, preferably from 4-12 hours, and the cycle is repeated until one or more teeth are successfully moved. More particularly, the orthodontic appliance of the invention has a vibrational source capable of providing a vibratory force at a frequency of between 20 to 40 Hz or 30 Hz and a force of 0.2 Newtons. Excess force is generally unpleasant to the patient, especially force coupled with high frequency, and in preferred embodiments these parameters are adjustable.

BRIEF DESCRIPTION OF THE DRAWINGS

FIG. 1A-D. Improved bite plate designs accommodating deep, flat and open bites.

FIG. 2A-D are perspective views of the bite plate with connector for attachment to extraoral vibrator. FIGS. 2A and 2B are the inner core and clear polymeric overcoat, in this prototype Versaflax CL2250. Also, shown in FIGS. 2C and 2D is a the inner core without the coating.

FIG. 5A is a perspective view of the core with battery, on/off switch and vibrators, where the hermetically sealed coating is omitted for clarity. FIG. 5B is a top view of an embodiment showing polymeric dividers between various portions of the bite plate to dampen the vibration between the segments (vibrator and other components omitted for clarity). 5C is a side view with clear coating.

DESCRIPTION OF EMBODIMENTS OF THE INVENTION

Figure 3A:
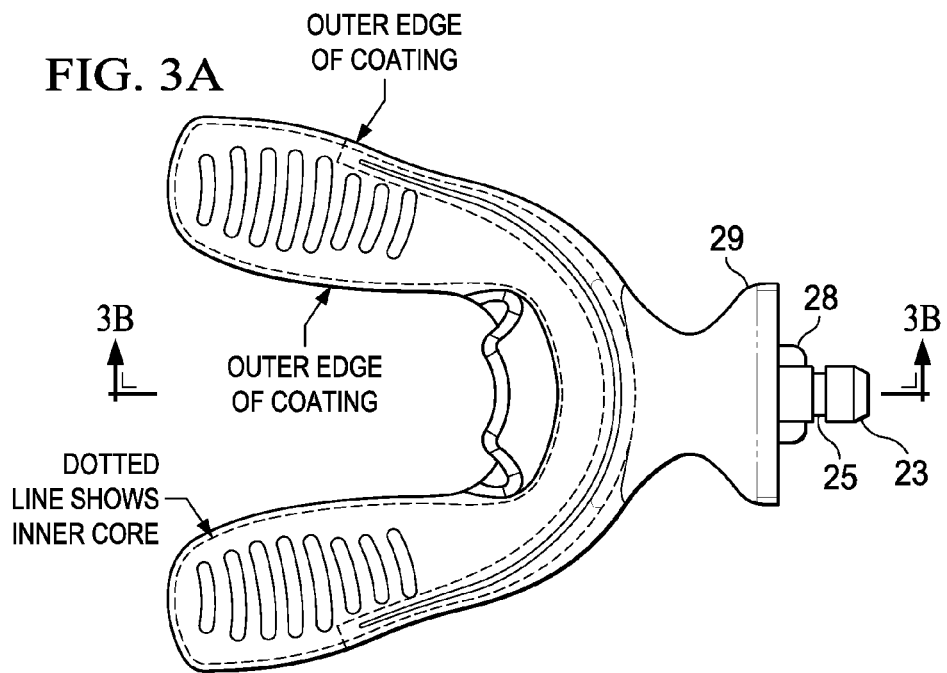
FIG. 3A-D are line drawings of the bite plate and connector, showing a flare, a shaft, pins and depression, groove and the spring that fits into the groove.
Figure 3B:
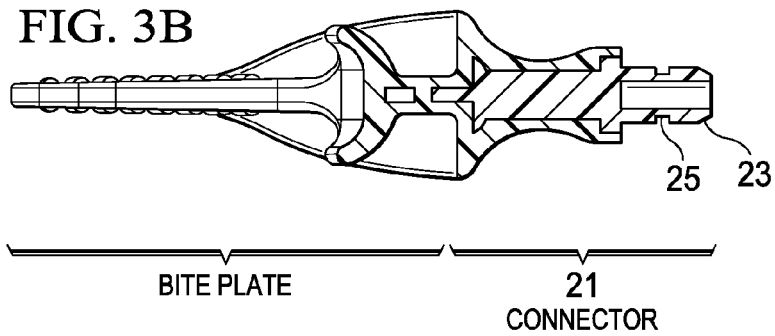
Figure 3C:
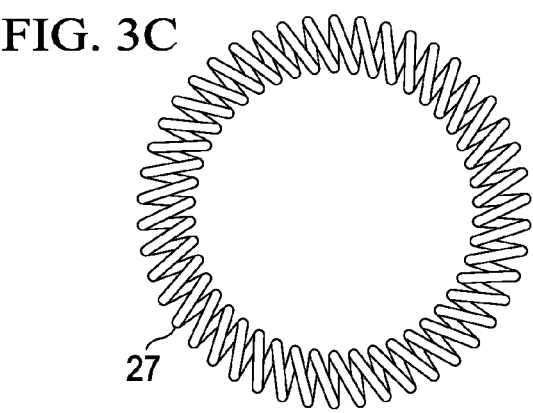
Figure 3D:
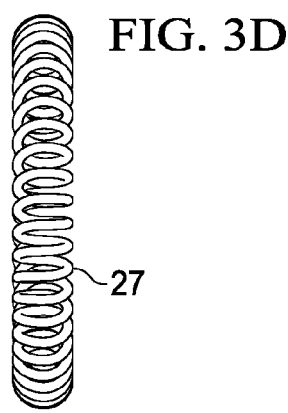
Figure 4A:
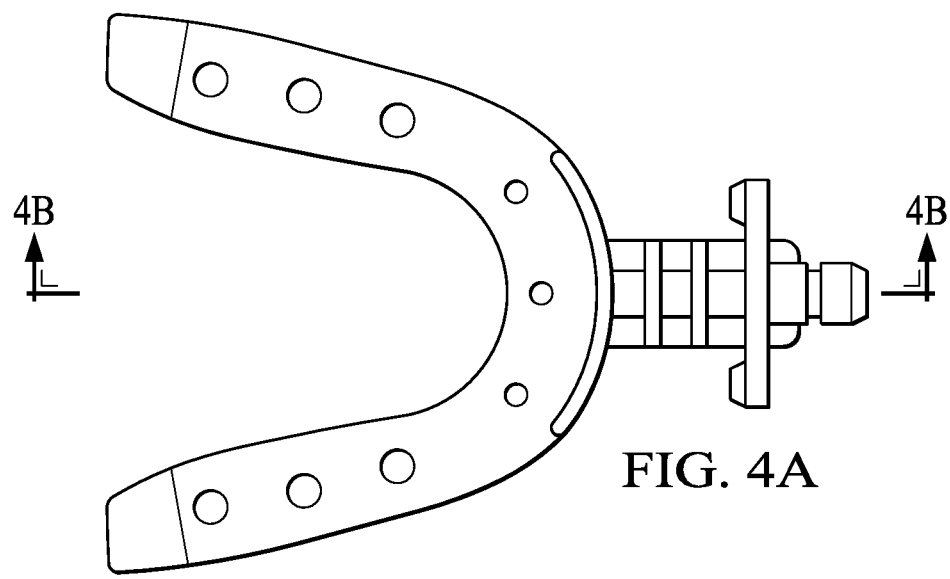
FIG. 4A-B show sizing details of the connector of FIG. 3.
Figure 4B:
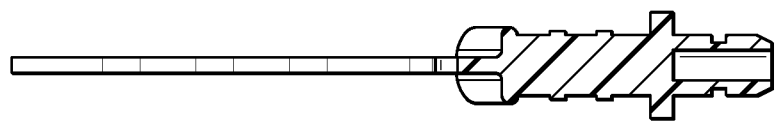

The following examples are illustrative only and not intended to limit the invention.

Example 1

The improved mouthpieces or bite plates are available in two sizes (small and large) based primarily on the anatomical dimensions of the patient's dental arches. Each size is available in three profiles based primarily on the type of malocclusion (open bite, deep bite and normal flat plane occlusion).

In the bite plates shown in FIG. 1, the phalanges that contact the lingual and buccal (inside and front) surface of the teeth are omitted for clarity, but such phalanges or edges are preferred since these edges allow greater contact with the teeth for improved comfort and improved transmission of the cyclic forces. Also shown in FIGS. 1A-D are optional ridges on the surface of the bite plate.

The sizes and profiles have been developed based on a statistical analysis of a sample population and are intended to allow for a maximum contact of teeth with the bite plate in a high percentage of patients and case types. The dimensions given in Table 1 are based on a minimum thickness E of 3.0-3.1 mm for the bite plate and based on using 6 sizes to fit most members of an average patient population. Obviously the final dimensions will change if the minimum thickness is changed (e.g., in an intraoral embodiment the thickness may increase to accommodate mechanical and/or electrical components), and customized bite plates may be required for outliers.

Generally speaking, the bite plate is U shaped, and can optionally have a connector at the midline to provide for secure attachment to an extraoral component. E represents the minimum thickness of the bite plate and ranges from 1-10 mm and preferably 2-5 mm or about 3 mm as in Table 1.

The thickness E increases from the ends of the U (where the molars would be when in use) towards the midline D (where the front teeth would be when in use) for use in patients having an open bite, and ranges from E to D=E+ 0.5-10 or more preferably 1-3 mm.

In the bite plate for the patient having a flat bite, the thickness E does not vary substantially from the molars to the anterior teeth.

For the patient having a deep bite, the bite plate is generally thicker at the molars (ends) than at the front (midline) (not shown) by 0.5-10 mm. Alternatively, the deep bite plate may have two portions of different thickness with the thicker portion being at or near the ends and the thinner portion at or near the front, but not vary within each portion (not shown). In one preferred embodiment, the thickness E increases 0.5-10 mm (or 1-3 mm) from the ends towards the middle, but then narrows and again is roughly flat at the front to accommodate the 4-6 anterior teeth.

The exterior width (perpendicular to the midline) of the U-shaped bite plate ranges from 62-70 mm and the length (along the midline) ranges from 51-53 mm. More particularly, the U shaped plate also has an interior width B between the ends of the U and an exterior width A that includes the width of the bite plate ends. Further, the bite plate has a length C from the ends to the base of the U. In the small bite plate, the interior width B is 30-32 mm and preferably 31.8-31.9 mm, and the exterior width A is 61-63 mm, preferably 62.6-62.7 mm. The length C ranges from 51-53 mm, preferably 52.1.-52.4 mm. In the larger bite plate, B is 36-39 or about 37.7, A is 68-70 or 69.9-70, and C is 51-52 or 51.5-51.9.

TABLE 1

Optimal bite plate dimensions all sizes in mm

| | Small | | | Large | | |
|---|---|---|---|---|---|---|
| | Open Bite | Deep Bite | Flat Bite | Open Bite | Deep Bite | Flat Bite |
| A | 62.6 | 62.6 | 62.7 | 69.9 | 69.9 | 70.0 |
| B | 31.9 | 31.9 | 31.8 | 37.8 | 37.8v | 37.8 |
| C | 52.1 | 52.4 | 52.1 | 51.9 | 51.9 | 51.5 |
| D | 5.3 | 3.5 | 4.4 | 5.3 | 3.5 | 4.3 |
| E | 3.1 | 3.1 | 3.1 | 3.1 | 3.1 | 3.0 |

In general, the bite plate should be the smallest size possible for patient comfort without impinging on the cheeks, tongue and/or interfering with orthodontic appliances. During the course of orthodontic care the patient may require additional bite plates due to wear, change in occlusion (particularly as the treatment plan corrects maligned dentition), or continued craniofacial growth. Therefore, the fit should be reevaluated at adjustment visits, particularly if the patient complains of poor fit or discomfort.

The bite plates can be sterilized using chemical or autoclaving methods as follows: 1) using full strength Centra Cidex 7 at room temperature for 10 hours; 2) Steam Sterilization with pre-vacuum: 3-4 minutes at 270° F. to 274° F. (132° C. to 134° C.) and 28-30 psi (193-207 kpa); 3) Steam Sterilization with gravity displacement: 20-30 minutes at 250° F. (121° C.) and 15-17 psi (104-117 kpa). Alternatively, only the sizing plates may be manufactured so as to withstand sterilization, and the customer bite plates can be of different materials.

Example 2

In a second embodiment, an improved extraoral vibrator has a more stable vibrator with improved performance characteristics of decreased sound and low variability frequency and force. In particular, the improved vibrator has a noise level less than 55 dB when measured at 6 inches, and preferably less than 50, 45, 40, or 35 dB. The improved vibrator provides a frequency at 20-40 Hz, preferably 30 Hz with a variance of only 2 Hz, and preferably 1 or 0.75 Hz. This is particularly important where the patient may move around during use, whereby lower quality vibrators may vary substantially with motion and/or orientation and thus provides an inconsistency that may be less efficacious, and may make FDA clearance of such a device more difficult. Further, the improved vibrator provides force at 0.1-0.5 Newtons, and preferably at 0.20 Newtons (20 grams) with a variance of ±0.05 N, and preferably less than ±0.03 N.

Consistency of frequency and force is achieved herein via a feedback loop whereby motor speed is monitored and software adjusts the motor as needed. More particularly, the motor contains an integrated encoder that provides multiple high and low signal outputs per every motor revolution. The software counts the time between every encoder event and compares this to the desired target (e.g., 30 Hz). Based on this comparison, the software then adjusts the pulse width modulation that is driving the motor to increase or decrease speed as appropriate to maintain the desired speed. Accurate controlling of speed also controls the force.

A DC 6V Motor having off-set weight and 8 line integrated encoder is known to provide these characteristics, but other vibrators may also provide these performance characteristics, and can be easily tested for same. Preferably the battery is a chargeable 100 mAh Li battery. Preferably, the motor is the Series 1506 DC Motor, by Micromo Electronics, Inc. (Part No. 1506N006SRIE2-8), and the battery is a 100 mAh Li-PO battery by Harding Energy (Part no. BAN-E601421).

Another improvement on the extraoral vibrating device is the provision of a charging stand that serves to dock the vibrator and charge it at the same time. The charging station also has a display and software so that the user can see the usage data. Thus, a dental profession (or parent) can determine whether the patient is using the device as intended. In one embodiment, the display shows the number of uses per week (for example 6/7=86%), the number of uses per month (25/30=83%)) and the total number of uses (145 uses).

Example 3

Figure 6A:
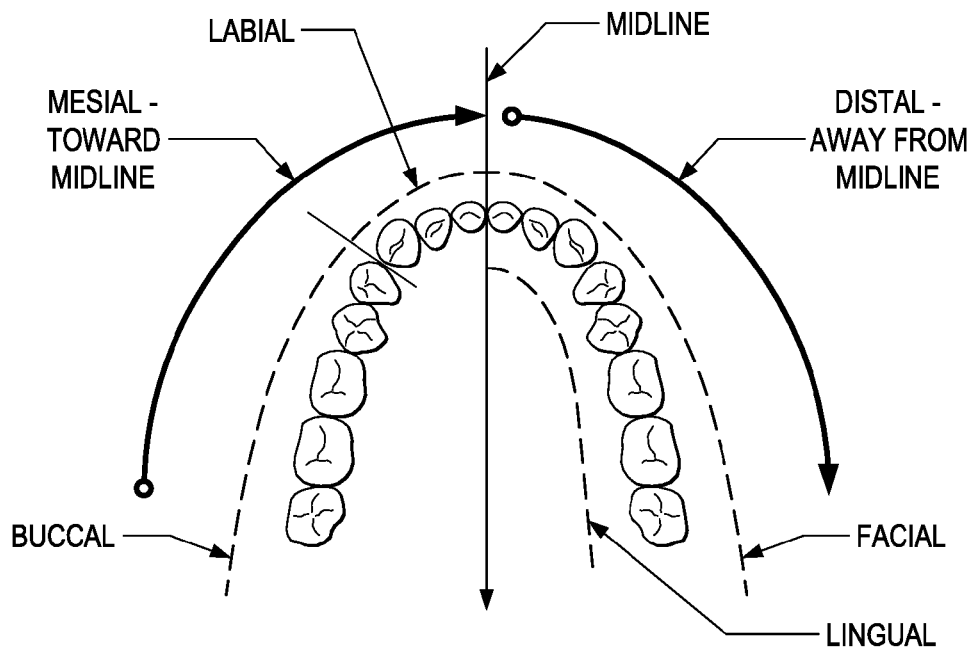
FIG. 6A-B provide basic dental nomenclature and is for reference purposes only.
Figure 6B:
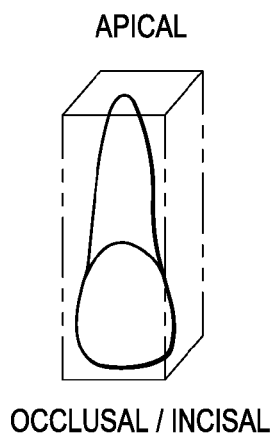

The bite plate of FIGS. 2A-D show the substantially U shaped bite plate 1 with clear overcoat 3 covering a stiff inner core 5 (shown as solid). Also shown is the lingual phalange or edge 7 for contacting the lingual surfaces of the teeth, in this instance only the front or anterior teeth (see labial area of FIG. 6A), and facial phalange 9 for contacting the facial surfaces of the teeth, as well as connector 2. The phalanges provide additional force transferring contacts with the teeth, but also aid in maintaining the correct position of the bite plate during use. Without the phalanges, the bite plate will vibrate away from the optimal position during use.

FIGS. 3A-D show the details of the bite plate of FIGS. 2A-D, and FIG. 4A-B includes sizing details of a preferred embodiment of the connector. In a basic configuration the connector 21 is a snap fit connector having a cylindrical shaft 23 that fits into a socket or receptacle on the vibrator. The shaft is of diameter 6-7 mm and preferably 6.35 mm (+0.03, −0.10). Further the shaft length is 5-15 mm, and preferably about 8-12 or 10.25 mm. In a preferred embodiment, the shaft is beveled at the end that fits into the socket to allow for easy insertion (not shown). A groove 25 in the shaft provides the snap fit, wherein a protrusion in the socket snap fits into the groove 25. The groove 25 is of width >1.4 mm, and depth ≥0.4 mm, and preferably is of width 1.65 mm and depth at least 0.4 mm, and preferably 0.425 mm (diameter at the groove is 5.5 mm). The groove 25 is positioned approximately midway (35-65%) along the groove, in this instance 4 mm from the bite plate end of the shaft. However, this distance from either end of the shaft 23 can be modified somewhat, depending on the length of the shaft 23, and yet the connector 21 will still fit into the same socket.

In this case, we designed a circular coil to spring fit into the groove, as shown, but any appropriately placed protrusions in the socket will suffice, including a protrusion that completely encompasses the circumference of the socket, or two or more small protrusions along the circumference of the socket and in alignment with said groove 25 (not shown). It is known in the art to vary the stiffness of the spring 27 to provide the appropriate degree of tension so that the bite plate is not inadvertently dislodged, yet is easily removed by the patient or dental professional.

Other features of the connector are shown, including pins on either side of the connector 21, and a flare 29 between the shaft 23 and the bite plate which has two depressions off center from the axis of the shaft 23 in order to prevent the bite plate from being inserted in the incorrect orientation. However, each of these features is exemplary and can be varied widely. For example, the protrusions (pins) 28 and depressions can be varied in number, placement and size, and the flare 29 is optional or can be differently shaped. Preferably, the flare 29 is shaped for easy handling with the thumb and fore finger and thus has the dumbbell shape as shown.

Example 4

Figure 7:
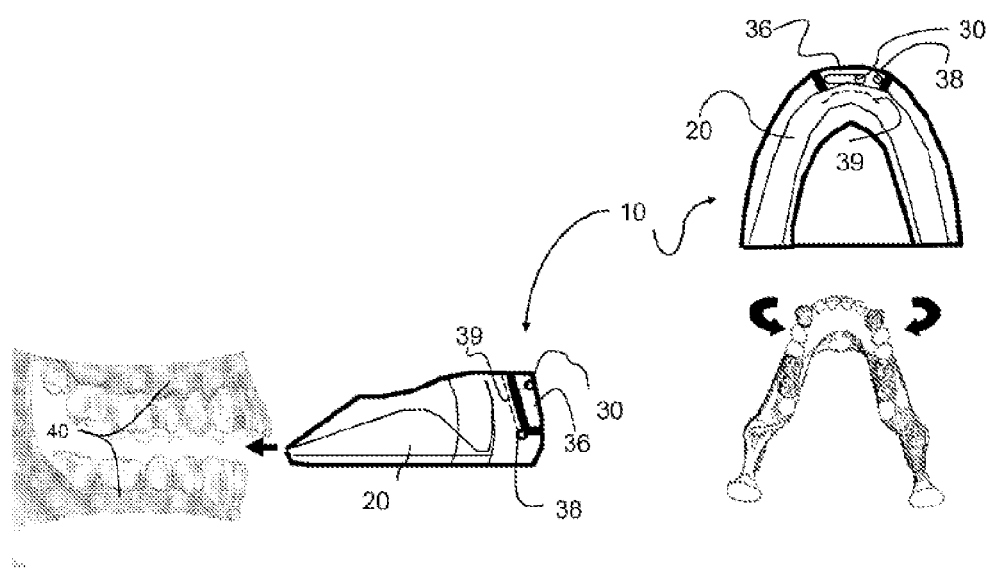
FIG. 7 shows an intraoral embodiment of the orthodontic treatment system.

The parent case describes an intraoral embodiment 10 shown in FIG. 7. Here, the vibration source 30 is positioned intraorally and holds the components necessary to generate and apply the force. This embodiment can generate and apply non-static forces to either the maxillary or mandibular arch or both. This particular embodiment involves a dual arch configuration that works with both dental arches 40. The patient inserts the plate 20 into the oral cavity and bites down, holding the system 10 steady between the teeth, regardless of which of the arches 40 the device is being activated for use with. The vibration source 30 contained in the intraoral compartment 36 is activated by pushing a button 38 mounted to the housing apparatus. The vibration source could be activated by sensing the patient bite pressure as stimuli with a microprocessor 39 or some other mechanism translating the external stimuli into device function.

In this embodiment, the device works when the patient applies sufficient force by biting on the device or otherwise clamping the jaws on the device. This enables the device to control the provision of cyclic forces when the correct amount of force is applied. In this embodiment, the device includes 1) microprocessor and compliance software and reporting system; 2) ability to provide cyclic forces at any level; and 3) the ability to only provide the cyclic force when the teeth apply the correct force on the device. An activation trigger can also be tied to some other stimuli including temperature or moisture sensing as well as salivary mineral content sensing.

Figures 5A, 5B:
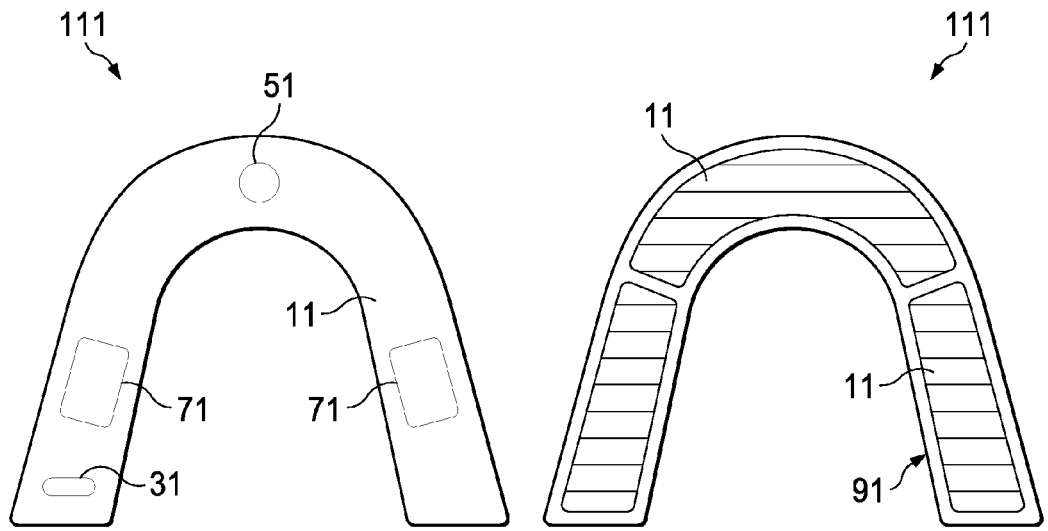
FIG. 5A-C show an intraoral bite plate in several views.
Figure 5C:
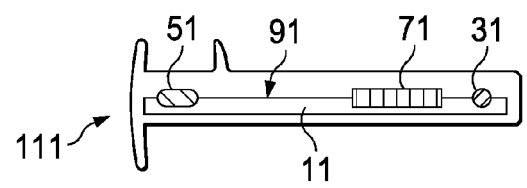

The intraoral device 111 of FIGS. 5A-C illustrate the core 11 having a battery 31, on/off switch 51, and two vibrators 71. The same device is shown in side view with the clear polymeric coating 91 to form the complete intraoral vibrating dental plate. The minimum intraoral device has an intraoral motor, and is activatable wirelessly (not shown). Thus, the battery and switch can be omitted. However, battery and various controllers can also be provided directly in the device as shown. Further, circuitry can be added to allow this device to store usage information and communication wirelessly with an external controller (not shown).

Another view in FIG. 5B shows an embodiment wherein segments of the inner core 11 (here shown three) are separated by portions of a polymeric material that serves to dampen vibration from one segment to the other, allowing the dental professional to vibrate 2, 3, 4, 5 or 6 segments of the device individually, thus customizing treatment for each patient. In this instance, the polymeric overcoat that seals the device is sufficiently soft and elastomeric to also provide the dampening function and thus the same material meets both needs. In other embodiments, two or more different materials are used.

In those embodiments where an external controller is provided for the intraoral bite plate, the controller or processor can provide one or more of the following functions: 1) wirelessly power and activate the vibrators; 2) differentially activate multiple vibrators; 3) synchronize multiple vibrators to have the same frequency and timing; 4) differentially control multiple vibrators to provide different forces; 5) wirelessly charge an internal battery; 6) wirelessly download and display usage information (or transmit such information to an external display); and 7) wirelessly identify the size of the plate. Preferably, the controller has a display and is programmed to provide the dental professional with a variety of usage options via a menu and/or data entry fields, but these functions can also be provided with yet another processor (e.g, a laptop computer) having increased display space and computing power, and the initial processor merely serves as a dedicated interface between the two.

Example 5

A pilot clinical study was performed by Chung How Kau, BDS, PhD with an extraoral vibrator and bite plate, as described herein. The study was conducted with 17 subjects, 14 of whom completed the study. Subjects with a Class I malocclusion and at least 6 mm of lower anterior crowding were provided with the device and instructed to use it for 20 minutes daily for six months during orthodontic treatment. Other selection criteria for the study included estimated level of compliance with use of the device in accordance with the instructions and good oral hygiene. Several subjects also required extractions and space closure.

Although compliance varied from patient to patient, patients reported using the device about 80% of the time, while the device microcomputer documented an average of 67% usage. No adverse events were reported during the study, and most patients watched television, listened to music, or played video games while using the device. The most common word used to describe device use was "easy."

A cone beam device (GALILEOS™ by SIRONA™) was utilized to accurately measure tooth roots and to estimate any resulting root resorption, with imaging in all three planes (sagittal, axial and coronal views). The study was designed to determine if any root resorption greater than 0.5 mm occurred or if there were alterations in root lengths, and no significant losses were found.

The study also measured distances between teeth using a digital caliper. The overall distance in millimeters between the front five teeth, both upper and lower, was calculated during the alignment phase. The gap between teeth due to extractions was measured directly. The overall movement rate during the study was 0.526 mm per week, which is higher than average movement without the device.

We conclude that the device increases the rate of orthodontic tooth movement and can be used with either fixed orthodontic appliances or clear aligners, offering flexibility. This is useful given the mix of orthodontic therapies available and particularly since some patients have combination therapy utilizing both fixed orthodontic appliances and clear aligner therapy. Short-term daily use for 20 minutes provides an advantage for patients.

The following references are expressly incorporated in their entirety:

US2006287620
US2007103016

US2007161461
US2007161931
US2007179414
US2007208284
US2007255188
US2007299372
US2008129130
US2008227046
US2009051312
US2009058361
US2009224616
U.S. Pat. No. 4,244,688
U.S. Pat. No. 4,348,177
U.S. Pat. No. 4,382,780
U.S. Pat. No. 5,030,098
U.S. Pat. No. 5,554,971
U.S. Pat. No. 5,780,958
U.S. Pat. No. 5,967,784
U.S. Pat. No. 6,632,088
U.S. Pat. No. 6,684,639
U.S. Pat. No. 6,832,912
U.S. Pat. No. 6,870,304
U.S. Pat. No. 7,029,276
WO200178217
WO2007116654

The invention claimed is:

1. A faster method of orthodontic remodeling, comprising:
   a) a patient wearing an orthodontic appliance biting an orthodontic remodeling device, said orthodontic remodeling device comprising:
      i) an extraoral housing containing a power source operably coupled to an actuator operably coupled to a processor that controls said actuator;
      ii) said extraoral housing operably connected to an intraoral U-shaped bite plate;
      iii) said bite plate having upper and lower vertical rims on a facial edge thereof to contact both arches of teeth; and
      iv) wherein during use said orthodontic remodeling device is held in place only by teeth clamping on the bite plate and said orthodontic remodeling device vibrates at a frequency from 0.1 to 400 Hz; and
   b) activating said orthodontic remodeling device for 1 to 20 minutes daily;
      wherein said method provides accelerated tooth movement as compared to without using said orthodontic remodeling device.

2. The method of claim 1, wherein said power source is a battery.

3. The method of claim 2, wherein said battery is a rechargeable battery.

4. The method of claim 2, wherein said battery is a rechargeable battery that is charged from a USB port.

5. The method of claim 1, wherein said orthodontic appliance comprises braces.

6. The method of claim 1, wherein said orthodontic appliance comprises an aligner.

7. The method of claim 1, said bite plate having upper and lower vertical rims on a lingual edge thereof.

8. The method of claim 1, wherein said orthodontic remodeling device automatically shuts off after 20 minutes.

9. The method of claim 1, wherein said orthodontic remodeling device vibrates at about 30 Hz and about 0.2 N and said accelerated tooth movement is about 0.5 mm per week.

10. A faster method of orthodontic remodeling, comprising:
    a) a patient wearing an orthodontic appliance biting an orthodontic remodeling device, said orthodontic remodeling device comprising:
       i) an extraoral housing containing a power source operably coupled to an actuator operably coupled to a processor that controls said actuator; and
       ii) said extraoral housing operably connected to an intraoral U-shaped bite plate;
       iii) wherein during use said orthodontic remodeling device is held in place only by teeth clamping on the bite plate and said orthodontic remodeling device vibrates at a frequency from 0.1 to 400 Hz; and
    b) activating said orthodontic remodeling device for 1 to 20 minutes daily;
       wherein said method provides accelerated tooth movement as compared to without using said orthodontic remodeling device.

11. The method of claim 10, wherein said power source is a battery.

12. The method of claim 11, wherein said battery is a rechargeable battery.

13. The method of claim 11, wherein said battery is a rechargeable battery that is charged from a USB port.

14. The method of claim 10, wherein said orthodontic appliance comprises braces.

15. The method of claim 10, wherein said orthodontic appliance comprises an aligner.

16. The method of claim 10, wherein said orthodontic remodeling device automatically shuts off after 20 minutes.

17. The method of claim 10, wherein said orthodontic remodeling device vibrates at about 30 Hz and about 0.2 N and said accelerated tooth movement is about 0.5 mm per week.

18. The method of claim 17, wherein said accelerated tooth movement is about 0.5 mm per week.

19. A faster method of orthodontic remodeling, comprising:
    a) a patient wearing an orthodontic appliance biting an orthodontic remodeling device, said orthodontic remodeling device comprising:
       i) an extraoral housing containing a power source operably coupled to an actuator operably coupled to a processor that controls said actuator and captures and communicates device usage data including duration of use and frequency of use; and
       ii) said extraoral housing operably connected to an intraoral U-shaped bite plate;
       iii) wherein during use said orthodontic remodeling device is held in place only by teeth clamping on the bite plate and said orthodontic remodeling device vibrates at a frequency from 0.1 to 400 Hz; and
    b) activating said orthodontic remodeling device for 1 to 20 minutes daily;
       wherein said method provides accelerated tooth movement as compared to without using said orthodontic remodeling device.

20. The method of claim 19, wherein said power source is a battery.

21. The method of claim 20, wherein said battery is a rechargeable battery.

22. The method of claim 20, wherein said battery is a rechargeable battery that is charged from a USB port.

23. The method of claim 19, wherein said orthodontic appliance comprises braces.

24. The method of claim 19, wherein said orthodontic appliance comprises an aligner.

25. The method of claim 19, wherein said orthodontic remodeling device automatically shuts off after 20 minutes.

26. The method of claim 19, wherein said accelerated tooth movement is about 0.5 mm per week.

27. The method of claim 19, wherein said orthodontic remodeling device vibrates at about 30 Hz and about 0.2 N and said accelerated tooth movement is about 0.5 mm per week.

* * * * *

(12) INTER PARTES REVIEW CERTIFICATE (2215th)
United States Patent
Lowe

(10) Number: US 9,662,184 K1
(45) Certificate Issued: Jul. 21, 2021

(54) VIBRATING DENTAL DEVICES

(71) Applicant: Michael K. Lowe

(72) Inventor: Michael K. Lowe

(73) Assignee: ADVANCED ORTHODONTICS AND EDUCATION ASSOCIATION, LLC

Trial Number:

IPR2018-00296 filed Dec. 15, 2017

Inter Partes Review Certificate for:

Patent No.: 9,662,184
Issued: May 30, 2017
Appl. No.: 15/186,958
Filed: Jun. 20, 2016

The results of IPR2018-00296 are reflected in this inter partes review certificate under 35 U.S.C. 318(b).

INTER PARTES REVIEW CERTIFICATE
U.S. Patent 9,662,184 K1
Trial No. IPR2018-00296
Certificate Issued Jul. 21, 2021

AS A RESULT OF THE INTER PARTES REVIEW PROCEEDING, IT HAS BEEN DETERMINED THAT:

Claims 1-27 are cancelled.

\* \* \* \* \*